United States Patent
Yakoub et al.

(10) Patent No.: US 11,202,906 B2
(45) Date of Patent: Dec. 21, 2021

(54) SKIN TREATMENT DEVICE AND METHOD FOR DELIVERY OF AN ACTIVE INGREDIENT INTO THE HUMAN SKIN BY MEANS OF IONTOPHORESIS, USING AN ARRAY OF ELECTRODES

(71) Applicant: FEELIGREEN SA, Valbonne (FR)

(72) Inventors: Abdelwahhab Yakoub, Antibes (FR); Christophe Bianchi, Nice (FR)

(73) Assignee: FEELIGREEN SA, Valbonne (FR)

(*) Notice: Subject to any disclaimer, the term of this patent is extended or adjusted under 35 U.S.C. 154(b) by 427 days.

(21) Appl. No.: 16/338,167

(22) PCT Filed: Sep. 27, 2017

(86) PCT No.: PCT/IB2017/001368
§ 371 (c)(1),
(2) Date: Mar. 29, 2019

(87) PCT Pub. No.: WO2018/060772
PCT Pub. Date: Apr. 5, 2018

(65) Prior Publication Data
US 2020/0023178 A1      Jan. 23, 2020

(30) Foreign Application Priority Data
Sep. 29, 2016   (GB) .................................. 1616547

(51) Int. Cl.
*A61N 1/04*      (2006.01)
*A61N 1/32*      (2006.01)

(52) U.S. Cl.
CPC .......... *A61N 1/325* (2013.01); *A61N 1/0432* (2013.01); *A61N 1/0476* (2013.01)

(58) Field of Classification Search
CPC ..... A61N 1/0432; A61N 1/0476; A61N 1/325
See application file for complete search history.

(56) References Cited

U.S. PATENT DOCUMENTS

| 4,406,658 A | 9/1983 | Lattin et al. |
| 5,954,684 A | 9/1999 | Flower et al. |
| 6,757,560 B1 | 6/2004 | Fischer et al. |
| 8,470,853 B2 | 6/2013 | Anderson et al. |
| 2006/0089674 A1* | 4/2006 | Walters .................. A61N 1/327 607/3 |

FOREIGN PATENT DOCUMENTS

WO      WO 02/24274 A1      3/2002

OTHER PUBLICATIONS

International Search Report as issued in International Patent Application No. PCT/IB2017/001368, dated Mar. 6, 2018.

* cited by examiner

*Primary Examiner* — Deanna K Hall
(74) *Attorney, Agent, or Firm* — Pillsbury Winthrop Shaw Pittman LLP

(57) ABSTRACT

A skin treatment device, adapted for delivery of an active ingredient into the human skin by means of iontophoresis, the device having electrodes to establish an electric field on the human skin, wherein the device includes an array of n electrodes with at least a first and a second electrode.

9 Claims, 4 Drawing Sheets

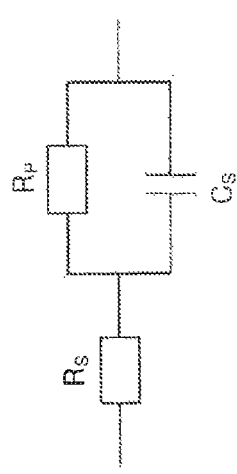
FIGURE 5
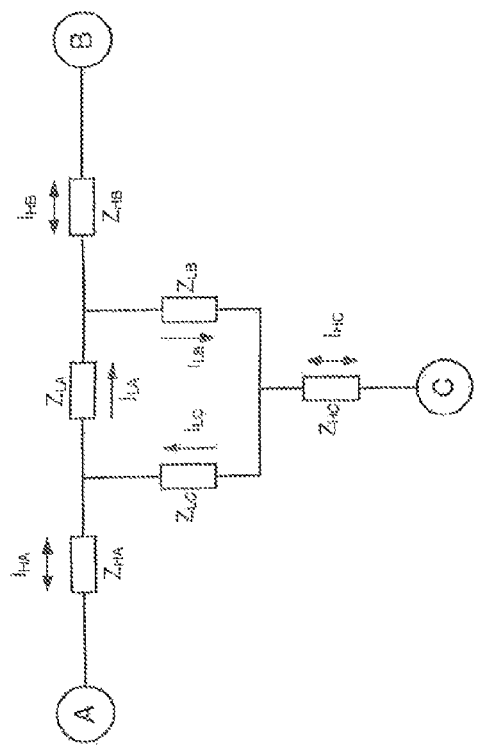
FIGURE 6
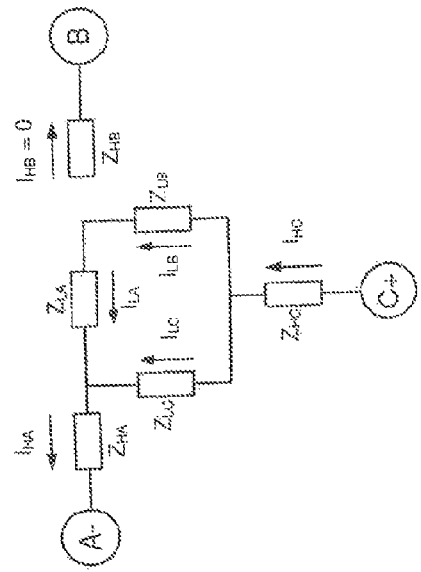
FIGURE 8
FIGURE 7

SKIN TREATMENT DEVICE AND METHOD FOR DELIVERY OF AN ACTIVE INGREDIENT INTO THE HUMAN SKIN BY MEANS OF IONTOPHORESIS, USING AN ARRAY OF ELECTRODES

CROSS REFERENCE TO RELATED APPLICATIONS

This application is the U.S. National Stage of PCT/M2017/001368, filed Sep. 27, 2017, which in turn claims priority to Great Britain Patent Application No. 1616547.4 filed Sep. 29, 2016, the entire contents of all applications are incorporated herein by reference in their entireties.

TECHNICAL FIELD

The technical field relates to a skin treatment device and a method for the delivery of an active ingredient into the human skin by means of iontophoresis using an array of electrodes. The electrodes are adapted to be connected to the human skin to apply an electric field to the human skin to thereby allow to deliver an active ingredient in the form of ions into the human skin.

BACKGROUND OF THE INVENTION

Iontophoresis is a physical process in which ions flow diffusively in a medium driven by an applied electric field. Iontophoresis can be used in therapeutic applications by applying an electric current on the skin using a pair of electrodes. On the skin, an active ingredient and solvent for said active ingredient will be present, wherein the positively charged electrode, called the anode, will repel a positively charged chemical species and wherein the negatively charged electrode, called the cathode, will repel a negatively charged species into the skin.

For the use of iontophoresis, electrodes have been developed wherein a first electrode is particularly adapted to be used as an anode and a second electrode is particularly adapted to be used as a cathode. During use a small electric current will be established between the anode and the cathode to stimulate the ions to pass through intact skin Despite the fact that iontophoresis has proven to be an efficient technology for electromotive drug administration, the known use of the first and the second electrode has a number of disadvantages. A first disadvantage is the fact that during the application of an electric field to the skin, in the contact area between the skin and the electrodes, the pH of the skin will be altered. Depending on the duration of the iontophoresis and the level of the electric field applied to the human skin, the pH of the skin will respectively increase/decrease at the anode/cathode to levels which can be unacceptable and which can lead to irritation of the skin. The fact that the pH can substantially alter during use of iontophoresis means that the use of iontophoresis is compromised in that the intensity of the current used and the period of time during which the iontophoresis is used can not exceed a certain threshold regarding the tolerability of iontophoresis for the human skin.

This is particularly troublesome because of the fact that one of the therapeutic uses for which iontophoresis is particularly useful is the application for anti-inflammatory medications.

A related problem of iontophoresis using a pair of electrodes is the fact that the electrodes are exposed to air which can lead to increased oxidation of the electrodes. This can lead to the electrode pair no longer being usable because of the high level of oxidation of at least one of the two electrodes.

In view of the above mentioned observations, the object of the present invention is to provide a method and a device for using iontophoresis wherein the disadvantages of methods and systems according to the prior art can be reduced.

SUMMARY OF THE INVENTION

According to a first aspect of the invention, the invention provides a skin treatment device adapted for delivery of an active ingredient into the human skin by means of iontophoresis, the device having electrodes to establish an electric field on the human skin, wherein the device comprises an array of n electrodes with at least a first and a second, wherein the device is adapted to successively establish an electric field between pairs of electrodes formed by a first electrode and a second electrode of said array of n electrodes, and wherein the device is adapted to form a subsequent pair of electrodes comprising one of the electrodes of a previous pair of electrodes and a further electrode selected from the array of n electrodes, wherein the device is adapted to inverse the polarity of the electrode used in both the previous pair and the subsequent pair prior to establishing an electric field with the subsequent pair of electrodes.

The applicants have noted that surprisingly, by using an array of electrodes having at least three electrodes wherein subsequently a first, second, and third electrodes are used for applying an electric field, lead to the effect that each of the electrodes serve subsequently as an anode, a cathode, an anode etc. The first effect is that the pH of the skin in contact with each of the electrodes will change during the use of the electrode in, for example, if used as an anode, but subsequently the pH will be allowed to return to a normal value with the electrode being used in a second function, such as the cathode. Alternating the polarity of the electrodes will avoid excess change of the pH in the contact area between the electrode and the human skin.

A related effect is the fact that the oxidation of one of a pair of electrodes is limited because of the fact that the polarity is changed. This means that the assembly of electrodes according to the present invention can be used during a longer time interval without losing its functionality.

According to a second aspect the invention relates to a method for delivering an active ingredient into the human skin by means of iontophoresis, the active ingredient having the form of ions to allow the active ingredient to be introduced into the skin by means of an electric field, wherein the method comprises the use of an array of n electrodes, n being an integer equal to or greater than 2, the array of electrodes being adapted to be connected to the human skin to apply the electric field to the human skin.

BRIEF DESCRIPTION OF THE DRAWINGS

The features and advantages of the present invention will be apparent from the detailed description of exemplary embodiments of the invention, making reference to the drawings, wherein:

FIG. 5 shows a simplified dynamic skin impedance model, FIG. 6 shows schematically, an electric representation of a system adapt for iontophoresis using a first, a second and a third electrode, FIG. 7 shows the electrical representation of FIG. 6 in case electrode C is disconnected.

FIG. 8 shows the electrical representation according to FIG. 6, in case electrode B is disconnected, FIG. 9 shows the result obtained by using a device wherein iontophoresis having a first, second and third electrode wherein the percentage of active ingredient that has passed a membrane is shown over a certain time interval.

For the description of the invention, all technical and scientific terms used herein have the same meaning as commonly understood by a skilled person.

The invention is described herein with respect to the treatment of skin, such as a human skin. It should be noted that the word skin makes reference to any human or animal barrier membrane including the skin or eye, oral, buccal, nasal, vaginal, gastrointestinal, or rectal mucosa.

Reference is made to a device for the treatment of the skin. The word "device" is meant to include the apparatus used for skin treatment as such or in a finished and packaged form. The device can contain a manual or instructions directing the user to apply the device to the human skin. Such instructions may be printed on the device or may be available on any additional packaging element.

The device is specifically adapted to treat the skin by using delivery of electricity to the skin and to thereby induce a desirable biological response of the tissue to which the electricity is delivered.

Figure 1:
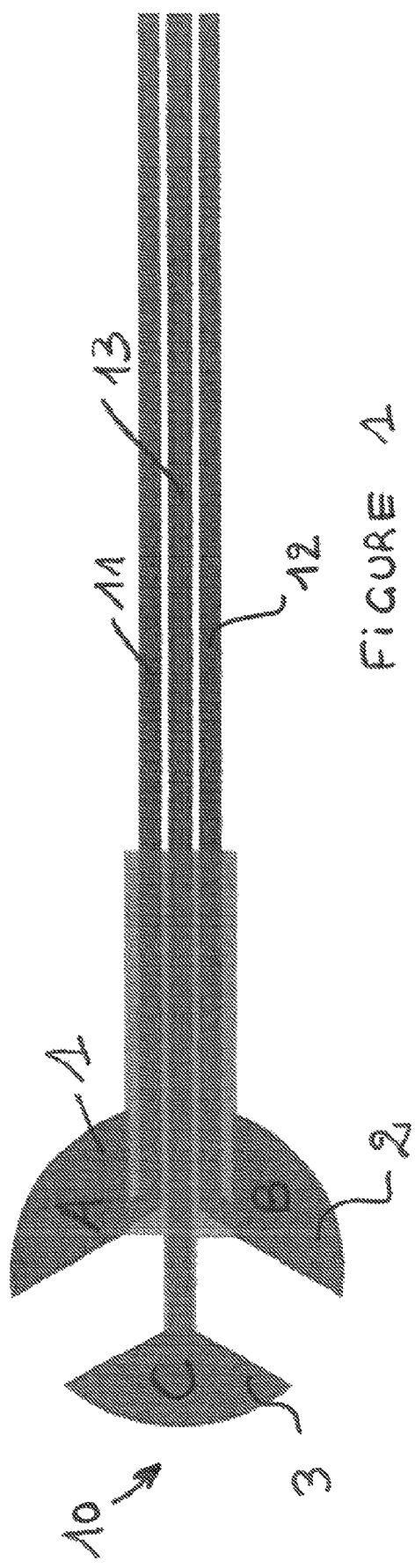
FIG. 1 shows a first exemplary embodiment of a skin treatment device having a first, a second and third electrode.

In FIG. 1, schematically, a device 10 is shown which is adapted for iontophoresis using an assembly of a first 1, second 2 and third electrode 3. A first electrode A has the form of a part of a circle and is connected to electrical wiring 12 to be connected to a source for electrical energy (not shown in FIG. 1). Similarly, a second electrode B is connected by means of electrical wiring 12 with a source for electrical energy. A third electrode C is connected by means of electrical wiring 13 with the source for electrical energy.

According to the example of FIG. 1, the electrodes A, B and C together enclose essentially a circular surface area wherein the electrodes A, B and C are spaced apart to allow the electrodes to be used as an electric couple for applying an electric field on the skin on which the device 10 is applied. According to the present invention, the first electrode A and the second electrode B can be used to apply an electrical field on the skin on which the device 10 is applied. In a first instance, the first electrode A serves as a positively charged anode. The second electrode B is used as a negatively charged cathode.

After a certain time interval, the electric field applied by using the first electrode A and the second electrode B, is interrupted. Subsequently, the second electrode B and a third electrode C are selected wherein an electric field is applied on the skin using the second electrode B and the third electrode C. When applying the electrical field, the second electrode functions as the positively charged anode wherein the third electrode C functions as the negatively charged cathode.

After a certain time period, the electrical field applied by the second electrode B and the third electrode C is interrupted. Subsequently, the third electrode C and the first electrode A are selected for applying an electric field on the human skin. When using the third electrode C and the first electrode A, the third electrode C functions as the positively charged anode wherein the first electrode functions as the negatively charged cathode.

It should be realized that the current when using the device 10 according to FIG. 1 always flows in the same direction whereby the polarity of each of the first, second and third electrodes changes with every change of selection of electrode paths. That means that upon contact with human skin on which the device 10 is connected, the polarity of, for instance, a first electrode is +, −, +, − etc.

A first effect of this measure is that the pH of the skin to which the device 10 is connected is not altered in a similar manner as when using an iontophoresis device according to the prior art. A second and related effect is that specific deterioration of either the anode or the cathode in the system for iontophoresis can be avoided since each of the electrodes A, B and C are subsequently anode, cathode, anode, cathode, etc.

In the example of FIG. 1, a device 10 for iontophoresis is shown having an assembly of a first 1, a second 2 and third electrode 3. It should be understood that the assembly could also comprise 4, 5 or more electrodes. The basic principal of the use of such a device is similar in that subsequently; electrodes are used, thereby allowing each of the electrodes to change in polarity when a new electrode pair is selected from the assembly of electrodes.

In the example of FIG. 1, the three electrodes 1, 2, 3 are positioned to enclosed essentially a circular surface area. In case an array of 4, 5 or more electrodes are used, a surface area in the form of for instance a square, a rectangle or an oval could be enclosed by means of the array of Inoval other surface area.

According to the embodiment of the invention the device could comprise a first 1 and a second 2 electrode. In that case the previous and subsequent pair of electrodes are formed by means of said first and second electrode. After the use of the previous pair of electrodes the electric field between the electrodes is interrupted. Thereafter, the polarity of both electrodes is inversed prior to establishing a further electric field between the first and second electrode.

In case the embodiment with a first and a second electrode is used, it is possible to use a first power signal for establishing an electric field between the previous pair of electrodes. After the inversion of the polarity of the electrodes, an opposite power signal will be used for establishing an electric field between the subsequent pair of the electrodes.

Figure 2:
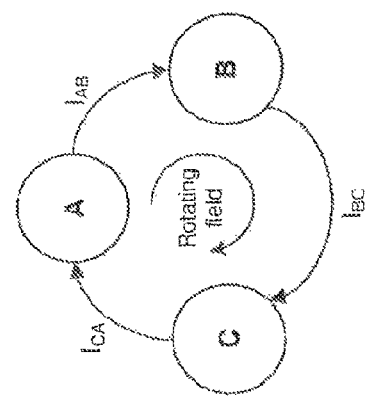
FIG. 2 shows schematically, a rotating electrical field between a first, a second and a third electrode.
Figure 3:
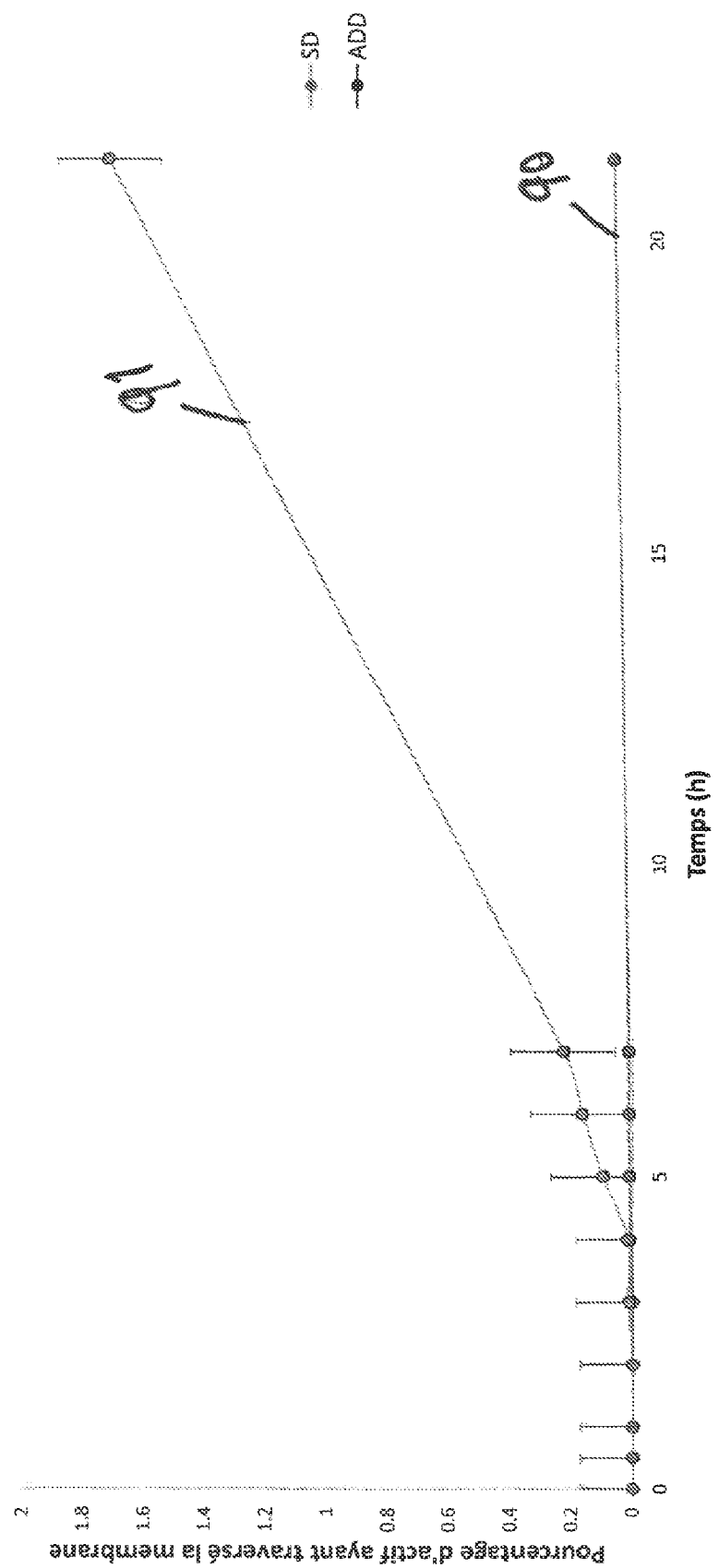

In FIG. 2, schematically, the three electrodes A, B and C are shown with the flow of a current being shown between each of the electrodes. The current $1_{ab}$ will flow when the electrodes A and B are selected to apply an electrical field on the human skin. With reference to FIG. 2, the device and system according to the present invention can be referred to as a system of iontophoresis by applying a rotational or alternating electric field around three or more electrodes.

In a three pole system, the electrodes can be arranged as shown below where A, B and C represent electrodes in the form of patches, and IAB, IBC and ICA represent the current resulting from the applied voltage between the patches.

The goal of MPSM is to apply a rotating current field by alternating the voltage between the patches as follows:

| IAB: (A+, B−) | IBC: (B+, C−) | ICA: (C+, A−) | IAB: (A+, B−) |
|---|---|---|---|

Figure 4:
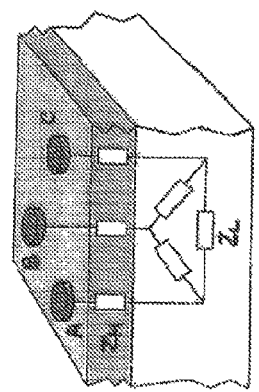
FIG. 4 shows schematically, the impedance of the skin when using iontophoresis by means of an array of electrodes with a first, a second and a third electrode.
Figure 3:
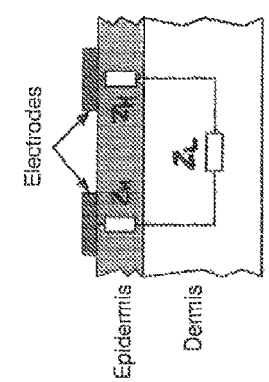
FIG. 3 shows schematically, the impedance of the skin when using iontophoresis using an assembly of a first and a second electrode.

In FIGS. 3 and 4 schematically, the impudence of the skin when using iontophoresis with two electrodes (FIG. 3) or three electrodes (FIG. 4) is shown.

The impedance of the epidermis ZH is high (of the order of 100 kW) and has a low capacitance (or the order of 10 pF).

The impedance of the dermis, ZL is lower (of the order of 10 kW) with a higher capacitance (of the order of 200 nF).

The model shown in FIG. 5 represents the system where the parameters Rs, RP, and CP are to be determined and Rs includes the active ingredient between the electrode and the skin.

The system then can be reduced to an electrical circuit represented in FIG. 6.

The objective is twofold:
1. Currents IHA, IHB, and IHC are to alternate in direction.
2. Currents ILA, ILB, and ILC should ideally be zero, but if non-zero their direction should not alternate.

Creating IHA, IHB, and IHC in an alternating fashion is achieved by controlling the electrode voltages:

| IHA positive | (A+, B−) with C = open circuit |
| IHA negative | (C+, A−) with B = open circuit |
| IHB positive | (B+, C−) with A = open circuit |
| IHB negative | (A+, B−) with C = open circuit |
| IHC positive | (C+, A−) with B = open circuit |
| IHC negative | (B+, C−) with A = open circuit | where positive direction is defined as from the electrode into the skin.

Note that IHA positive=IHB negative.

Given that the impedances ZH and ZL are inaccessible being the impedance of the skin itself, a fundamental problem arises in that the current ILx can never be zero, nor unipolar for a bipolar IHx current.

FIG. 7 shows the system with positive and negative IHA current. Wherein the positive IHA current with electrode 'C' is disconnected. Note that, 'disconnected' here means a very high (several MW) resistance added in series to the electrode.

In this arrangement, ZLB and ZLC are in series and their combination is in parallel with ZLA. Assuming that ZLA=ZLB=ZLC, then two thirds of IHA will flow in ZLA and one third flows in the series combination of ZLB+ZLC in the directions shown.

FIG. 8 shows, for the negative going IHA, electrode 'B' is disconnected while 'C' is positive with respect to 'A'.

In this arrangement, ZLA and ZLB are in series and their combination is in parallel with ZLC. Therefore two thirds of IHC will flow in ZLC and one third flows in the series combination of ZLA+ZLB in the directions shown.

Important to note here is, if we assume that IHA=IHC then for IHA positive, the magnitude of the current in ZLA is greater than the current in ZLA when IHA is negative (by a factor of two for ZLA=ZLB=ZLC). Therefore there is always a net positive current in ILA equal to ⅓ IHA.

In FIG. 9, the first table as shown with results when using a device 10 according to the present invention, compared to a system known in the prior art.

In FIG. 9, with a first curve 19, the percentage of active ingredient able to transfer through a membrane is shown over a time period of about 20 hours. As shown in FIG. 9, less than 0.2 percent of the active was able to pass through the membrane.

With curve 91, the system according to the present invention is shown during the same time frame of about 20 hours. FIG. 9 shows that the percentage of active which has been able to transfer has been dramatically increased to about 1.7 percent.

The present invention has been referred to as using an array of electrodes wherein subsequently electrode pairs (1-2), (2-3), (3-1) are used.

Alternatively or preferably, in addition to the use of multiple electrodes, it is possible to alter the specific current that has been used between a first and a second electrode.

Figure 10:
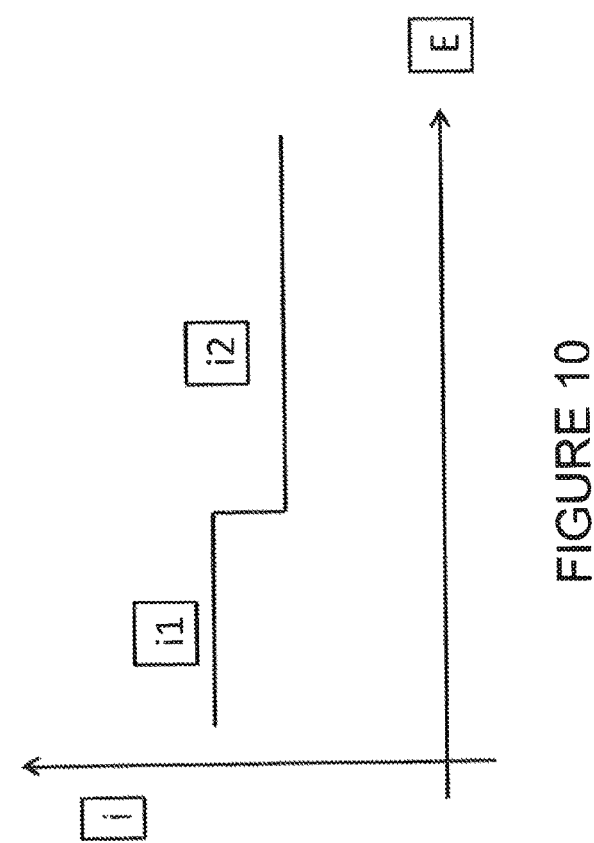
FIG. 10 shows the intensity of current used in the system for iontophoresis over a certain time period according to the prior art.

In the prior art, it is known that a specific delivery of active ingredients in the skin can be increased by applying a specific current density. U.S. Pat. No. 8,470,853 discloses a method for treating humans for migraine by means of patches, wherein said patches use a first current density and a second current density selected such that said first current density and said second current density do not essentially irritate the human skin. In FIG. 10 schematically, the use of a first and second fixed and continuous current density, according to the disclosure of U.S. Pat. No. 8,470,853 as shown.

Figure 11:
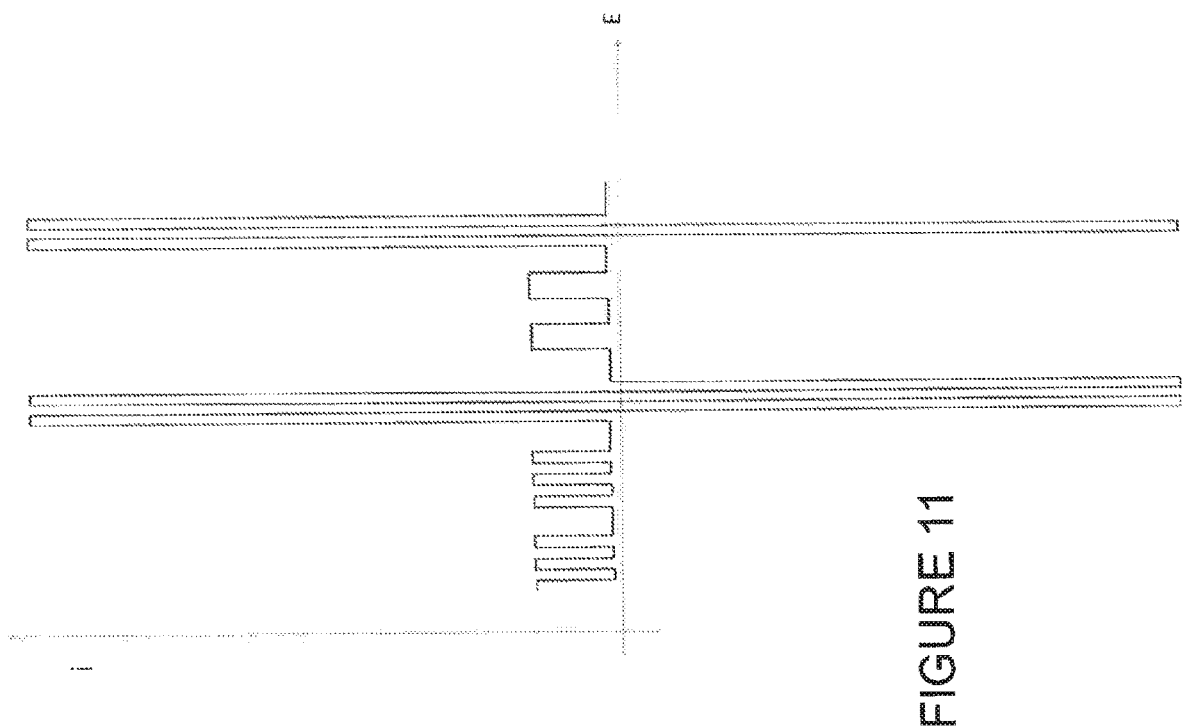
FIG. 11 shows the intensity of current used over time according to the present invention.

According to the present invention, the use of a first and a second current density means that contrary to the prior art, not a fixed and continuous current density is used, but rather pulses, which are in a programmable sequence according to a desired dose. This means that depending on the parameters indicative for the human skin and the active ingredient that is to be delivered into the human skin, a desired dose is obtained. In a further step, based on the desired dose for delivery of the active ingredient, a pattern for providing electrical pulses is obtained, wherein the length of the pulses and the intensity of the pulses allow the dose to be varied and allow for adaptation of the current density to the tolerability of the human skin. An example of such pulsed dose to be applied according to the present invention is shown in FIG. 11.

The invention claimed is:

1. Skin treatment device, adapted for delivery of an active ingredient into the human skin by means of iontophoresis, the device having electrodes to establish an electric field on the human skin, wherein the device comprises an array of n electrodes with at least a first and a second electrode, wherein the device is adapted to successively establish an electric field between pairs of electrodes formed by a first electrode and a second electrode of said array of n electrodes, and wherein the device is adapted to form a subsequent pair of electrodes comprising one of the electrodes of a previous pair of electrodes and a further electrode selected from the array of n electrodes, wherein the device is adapted to inverse the polarity of the electrode used in both the previous pair and the subsequent pair prior to establishing an electric field with the subsequent pair of electrodes, wherein the device is adapted to successively form a pair of electrodes with the first and the second electrode of said array of n electrodes, the second and a third electrode of said array of n electrodes, until the pair comprises electrodes n−1 and n, wherein the device is adapted to subsequently form a pair of electrodes with electrode n and the first electrode.

2. The skin treatment device according to claim 1, wherein the electrodes of said array of n electrodes are positioned equidistantly with respect to each other.

3. The skin treatment device according to claim 1, wherein the electrodes are positioned to enclose a surface area.

4. The skin treatment device according to claim 1, wherein the electrodes of the array of n electrodes are positioned to together form a circle.

5. The skin treatment device according to claim 1, wherein the device comprises a control system adapted to provide electrical power to the electrodes in the form of programmable pulses.

6. Method for delivering an active ingredient into the human skin by means of iontophoresis, the active ingredient having the form of ions to allow the active ingredient to be introduced into the skin by means of an electric field, wherein the method comprises the use of an array of n electrodes, n being an integer equal to or greater than 3, the array of n electrodes being adapted to be connected to the human skin to apply the electric field to the human skin, the method comprising the following steps:
   a) selecting a first and a second electrode from said array of n electrodes to form a pair of electrodes and establishing an electric field between the electrodes of said pair of electrodes, said pair of electrodes comprising respectively an anode and a cathode,
   b) after a determined time period, interrupting the electric field between the electrodes of said pair of electrodes,
   c) selecting one of the electrodes of a previous pair of electrodes and a further electrode selected from the array of n electrodes, to form a subsequent pair of electrodes,
   d) inversing the polarity of the electrode used in both the previous pair and the subsequent pair prior to establishing an electric field with the subsequent pair of electrodes and establishing an electric field between the electrodes of the subsequent pair of electrodes,
   e) after a determined time period, interrupting the electric field between the electrodes of said subsequent pair of electrodes,
   wherein the method comprises successively forming a pair of electrodes with the first and the second electrode of said array of n electrodes, the second and a third electrode of said array of n electrodes, until the pair comprises electrodes n−1 and n, and then subsequently forming a pair of electrodes with electrode n and the first electrode.

7. The method according to claim 6, wherein the method further comprises:
   f) repeating steps c), d) and e) for a determined time period.

8. The method according to claim 6, wherein the electrodes are positioned to together enclose a surface area, wherein the method comprises:
   a') selecting a first and an adjacent second electrode from said assembly of n electrodes to form a pair of electrodes and establishing an electric field between the electrodes of said pair of electrodes, said pair of electrodes comprising respectively an anode and a cathode,
   b') after a determined time period, interrupting the electric field between the electrodes of said pair of electrodes,
   c') selecting the second electrode of the pair of electrodes to form the first electrode of a subsequent pair of electrodes and selecting an adjacent electrode to said first electrode of said subsequent pair of electrodes from said array of n electrodes to form the second electrode of said subsequent pair of electrodes,
   d') inversing the polarity of the first electrode of the subsequent pair of electrodes and establishing an electric field between the electrodes of said subsequent pair of electrodes,
   e') after a determined time period, interrupting the electric field between the electrodes of said subsequent pair of electrodes, and
   f) repeating step c'), d') and e') for a determined time period.

9. The method according to claim 6, wherein the method further comprises:
   g) controlling the electrical field established between a pair of electrodes by means of programmable electrical pulses.

* * * * *